United States Patent [19]

Floyd

[11] 4,236,518
[45] Dec. 2, 1980

[54] CRYOGENIC DEVICE SELECTIVELY OPERABLE IN A CONTINUOUS FREEZING MODE, A CONTINUOUS THAWING MODE OR A COMBINATION THEREOF

[75] Inventor: James K. Floyd, La Canada, Calif.

[73] Assignee: Gyne-Tech Instrument Corporation, Burbank, Calif.

[21] Appl. No.: 896,495

[22] Filed: Apr. 14, 1978

[51] Int. Cl.³ .................. A61F 7/00; A61B 17/36
[52] U.S. Cl. .................. 128/303.1; 62/293; 137/630.19; 137/614.14
[58] Field of Search ............. 128/303.1, 399, 400, 128/401; 62/293, 514 JT; 137/630.19, 614.14; 251/77

[56] References Cited

U.S. PATENT DOCUMENTS

| | | | |
|---|---|---|---|
| 1,494,747 | 5/1924 | Jenkins | 137/630.19 |
| 2,787,294 | 4/1957 | Carridl | 251/77 |
| 3,272,203 | 9/1966 | Chato | 128/303.1 |
| 3,289,424 | 12/1966 | Shepherd | 128/303.1 |
| 3,393,679 | 7/1968 | Crump et al. | 128/303.1 |
| 3,696,813 | 10/1972 | Wallach | 128/303.1 |
| 3,794,039 | 2/1974 | Kollner et al. | 128/303.1 |
| 3,807,403 | 4/1974 | Stumpf et al. | 128/303.1 |
| 3,827,252 | 8/1974 | Chovet et al. | 62/514 JT |
| 3,913,581 | 10/1975 | Ritson et al. | 128/303.1 |
| 4,015,606 | 4/1977 | Mitchiner et al. | 128/303.1 |
| 4,063,560 | 12/1977 | Thomas et al. | 128/303.1 |
| 4,146,030 | 3/1979 | Holroyd | 128/303.1 |

Primary Examiner—Robert W. Michell
Assistant Examiner—Arthur S. Rose
Attorney, Agent, or Firm—Sellers and Brace

[57] ABSTRACT

A cryogenic device utilizing pressurized coolant gas and provided with a single control easily manipulatable by finger pressure to selectively furnish either continuous freezing or continuous thawing, each alone or in sequence. The expansion chamber is pressurized only when the control lever is deliberately held depressed and, in consequence, either the expansion chamber or the coolant inlet subassembly can be detached or exchanged without risk to the operator or the equipment and without need for closing off the coolant supply. A pressure regulator forming a part of the device limits the maximum possible pressure in the expansion chamber and exhaust passages to a safe value. The device is substantially noiseless in operation and the control is operable through first and second stages by movement in the same direction to provide freezing or warming modes at the user's option and is self-locking in the freezing mode but is automatically disengaged therefrom upon movement into the thawing mode.

44 Claims, 8 Drawing Figures

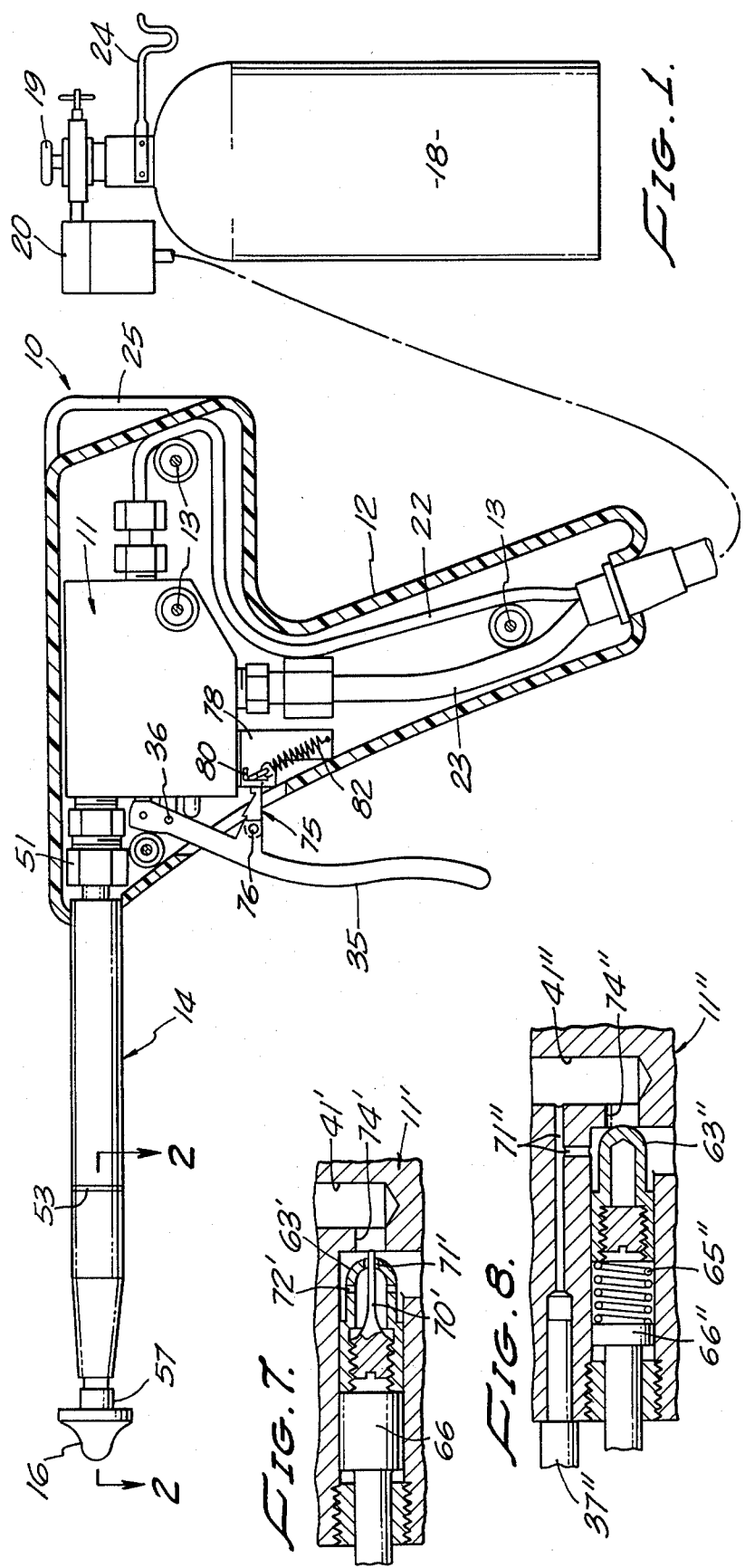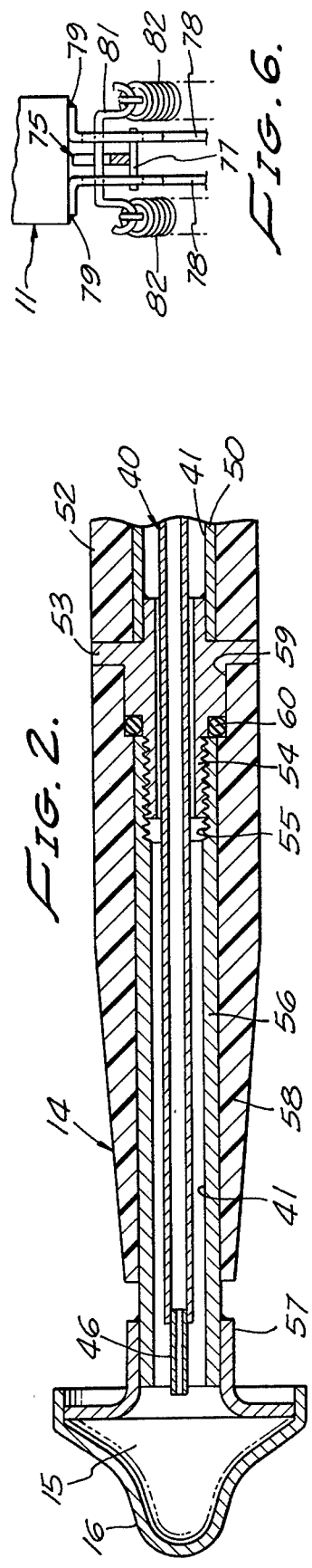

CRYOGENIC DEVICE SELECTIVELY OPERABLE IN A CONTINUOUS FREEZING MODE, A CONTINUOUS THAWING MODE OR A COMBINATION THEREOF

This invention relates to cryogenic devices, and more particularly to a unique, hand-held device equipped with a single finger-operated control movable through first and second stages to provide continuous freezing or continuous thawing, alone or in rapid or interrupted sequence utilizing only a source of pressurized gas.

BACKGROUND OF THE INVENTION

During recent decades there has been a surge of activity in the use of both low temperature liquids and pressurized gases to perform a variety of operations at sub-freezing temperatures. The activity of this field has been particularly pronounced in devices designed for cryosurgery purposes on both human and animal life. Designers and users of such equipment are confronted with numerous problems for which fully satisfactory solutions have not been achieved. Devices using high pressure gases have the decided advantage that the gas can be stored indefinitely at room temperature in a container of adequate strength. Such storage chambers are commonly pressurized to 800 lbs. or 1,000 lbs. or more and this presents a problem and hazards if such high pressure gas is released into an expansion chamber designed for contact with living tissue to be treated and desirably formed of thin-walled material having excellent heat conductivity. Another major problem involves the low heat conductivity of frozen tissue making it difficult to freeze to a depth of more than a few millimeters during a single freezing cycle. After thawing, frozen tissue may be removed to facilitate another freezing cycle but this necessitates appropriate provision for interrupting the operation of the cryogenic device and providing suitable means for thawing and removing the frozen tissue.

Another particularly serious problem involves the control of the high pressure gas which typically has necessitated the application of objectionably high manual operating forces to manipulate the controls, the need for applying these control forces over a prolonged period, the highly objectionable noise heretofore inherent in the operation of these controls along with the accompanying shock and vibration associated with the opening and closing of high pressure valves. These problems have seriously interfered with the use of cryosurgery devices in performing delicate operations on the brain, eye, ear and the like.

Typical patents disclosing structures subject to the numerous short-comings of the prior art include U.S. Pat. Nos. Hart 3,495,419; Amoils 3,502,081; Crump et al. 3,512,531; Reynolds et al. 3,548,829; Wallach 3,696,813 and 4,018,227; Stumpf 3,807,403; Ritson 3,913,581. Hart has a simplistic design utilizing pressurized gas and operable only in a freezing mode. Amoils discloses a much more sophisticated device employing an electric heater for defrosting and a thermocouple in the expansion chamber to measure temperature. Crump et al., Reynolds et al., the earlier Wallach patent and Stumpf each employ an exhaust valve effective to provide momentary or short duration defrosting capability at the end of a freezing cycle. In both Crump et al,. and Reynolds et al., the exhaust valve is normally closed with the result that the expansion chamber is pressurized at the pressure of the supply source which is hazardous to both the equipment and personnel for obvious reasons. Both Ritson and the later Wallach patent utilize normally open exhaust valves operable to provide short duration defrosting and including provision for purging the gas supply orifice opening into the expansion chamber.

SUMMARY OF THE INVENTION

This invention avoids the numerous short-commings and disadvantages of the above and other prior art proposals. An illustrative embodiment of the invention herein disclosed comprises a lightweight instrument of pistol-like configuration having a trigger-like control lever beside the hand grip operable through first and second stages. The first stage opens the normally closed inlet valve to supply high pressure gas coolant to an orifice discharging into the expansion chamber at the forward end of the instrument. The low pressure expanded gas escapes to the atmosphere from this expansion chamber via a venting passage provided with a normally open exhaust valve and a bleeder orifice of smaller capacity than the inlet orifice to the expansion chamber. First stage movement of the control locks the inlet valve open, the inlet valve being biased closed by a spring providing a force stronger than that required to hold the valve closed against the high coolant source pressure. Movement of the control through the second stage closes the exhaust valve which then functions as a low pressure regulator and allows warm gas from the tank to pass through the expansion chamber at a rate effective to operate the instrument probe in a continuous thawing or warming mode so long as the exhaust valve is held closed. The higher pressure prevailing in the expansion chamber during the thawing mode is utilized to counteract the spring pressure tending to close the inlet valve with the result that light finger pressure applied to the control suffices to maintain the instrument in the thawing or warming mode. The need for holding the control depressed during thawing is a safety feature precluding the possibility of the expansion chamber and exhaust passages being pressurized except when the control lever is deliberately gripped and depressed by the user to close the exhaust valve. This feature makes it feasible to exchange expansion chambers as well as the inlet orifice subassembly without risk since no part of the instrument can possibly be pressurized unless the exhaust valve is deliberately held closed.

Accordingly, it is a primary object of this invention to provide a cryogenic unit utilizing a pressurized gas coolant to provide continuous freezing or continuous thaw, along or in sequence, employing a single control easily operated with finger pressure.

Another object of the invention is the provision of a simply constructed lightweight pistol-like cryogenic unit having a flexible coolant inlet and outlet hose opening through the end of the hand grip and controlled by a trigger selectively operable through two ranges to provide freezing or thawing.

Another object of the invention is the provision of a cryogenic device operating with pressurized gas having means for utilizing the gas pressure to greatly minimize the control operating forces and wherein slight finger pressure suffices to operate both the coolant inlet valve and the exhaust control valve.

Another object of the invention is the provision of a hand-held cryogenic device utilizing a servo-mechanism responsive to gas pressure to minimize the manual operating forces thereby avoiding acoustical and mechanical shocks and greatly minimizing muscular and nervous strain on the operator.

Another object of the invention is the provision of a cryogenic instrument instantly convertible between continuous freezing, defrosting, and continuous warming modes, with or without intervening delay, and in any desired sequence.

Another object of the invention is the provision of a simple hand-held cryogenic instrument having a simple control for rapidly cycling the same through freeze-thaw modes thereby providing greatly expedited and lethal cryogenic tissue destruction in a time period and to depths not feasible heretofore.

Another object of the invention is the provision of a hand-held cryogenic device having a finger-control automatically lockable in a continuous freeze mode thereby enabling the physician to relax and concentrate on positioning the freezing element relative to the tissue under treatment and which locking means is instantly releasable by light finger pressure.

Another object of the invention is the provision of a cryogenic device having a pressurized coolant supply discharging through an orifice into an expansion chamber normally vented to the atmosphere and which coolant supply is normally closed by a spring biased valve whereby the vented expansion chamber poses no hazard if the inlet valve opens accidentally in response to an abnormal rise in the coolant supply pressure.

These and other more specific objects will appear upon reading the following specification and claims and upon considering in connection therewith the attached drawing to which they relate.

Referring now to the drawing in which a preferred embodiment of the invention is illustrated:

FIG. 1 is a side elevational view of an illustrative embodiment of the invention;

FIG. 2 is a cross-sectional view on an enlarged scale taken along line 2—2 on FIG. 1;

FIG. 6 is a fragmentary cross-sectional view taken along line 6—6 on FIG. 3;

FIG. 7 is a fragmentary cross-sectional view of a second embodiment of the exhaust valve; and FIG. 8 is a fragmentary cross-sectional view of a third embodiment of the exhaust valve.

Figure 3:
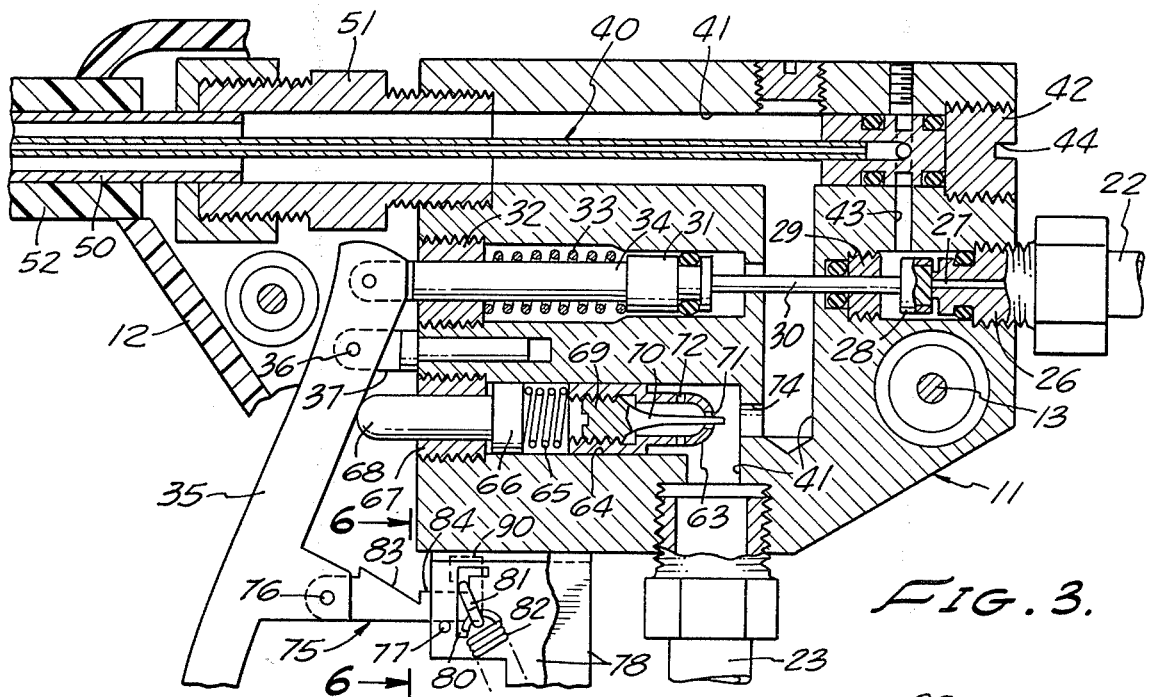
FIG. 3 is a cross-sectional view on an enlarged scale taken through the control mechanism showing the inlet valve closed and the exhaust valve open.

Referring initially to FIG. 1, there is shown a pistol-shaped embodiment of the invention cryogenic unit, designated generally 10, wherein the main body 11 of the valve mechanism is enclosed between the two halves of the plastic hand grip 12 by assembly screws 13. The instrument barrel 14 is provided with an expansion chamber 15 enclosed by a suitably shaped probe 16 of heat conductive material, such as silver. The instrument is connected to a conventional source of high pressure nitrogen gas or carbon dioxide gas, such as a tank 18, provided with a valve fitting 19 at its upper end which opens into a muffler 20 of known construction.

This muffler is provided with a pair of concentric flexible tubes the inner one 22 of which conveys pressurized coolant gas to the instrument and the outer one 23 of which conveys exhaust gas to the atmosphere by way of muffler 20. These tubes enter the lower end of the hand grip 12. Tank 18 is provided with a hanger 24 the outer end of which is shaped to freely receive the eyelet 25 at the inlet end of the instrument whereby the instrument may be safely hung from hanger 24 when not in use.

Referring now to FIG. 3, it is pointed out that the high pressure coolant, typically at 800 to 1,000 psi enters the main body casting 11 through a gasketed fitting 26 having a small bore inlet orifice 27 normally closed by a poppet valve 28 having its stem 30 slidably supported in bushing 29. The left-hand end of the valve stem abuts but is not connected to the adjacent end of a pressure responsive servo-piston 31 equipped with a sealing ring and slidably supported in a bushing 32. This piston is urged to the right to hold the valve 28 normally closed by a calibrated spring 33. This spring has a spring rate of 150 lbs. per inch and is sufficiently strong to maintain poppet valve 28 closed over the gas inlet port 27. The outer end of piston rod 34 is pivotably connected to the upper end of the control trigger or operating lever 35 which trigger is fulcrumed on a pin 36 supported on the bifurcated outer end of a bracket 37 fixed to main body 11.

The hollow barrel 14 of instrument 10 is provided with a coolant delivery tube subassembly 40 extending coaxially of its interior, this subassembly being detachably and removably supported in the right-hand end of the coolant venting passage 41 by a fluidtight bushing assembly 42. This bushing has an annular passage between its two fluid seals communicating with the gas inlet duct 43 and its threaded outer end portion is provided with a tool seating kerf 44. The downstream end of delivery tube sub-assembly 40, best shown in FIG. 2, is equipped with a coolant orifice 46 opening into expansion chamber 15 and having a port of suitable size as, for example, 0.016, 0.018 inches or the like. However, various other sizes are also suitable. The pressure drop occurring as the gas issues from orifice 46 producing low freezing temperatures in the expansion chamber 15 in accordance with the well known Joule-Thomson effect so long as the exhaust valve to be described presently is open.

As is best shown in FIG. 2, the instrument barrel 14 comprises an inner liner tube 50 coupled by fitting 51 (FIG. 1) to the main body 11 and shrouded on its exterior by a plastic or the like tube 52. A flanged fitting 53 is brazed or otherwise secured to the left-hand end of tube 50 and is provided with a threaded shouldered shank 54 mating with the threads 55 of a tube 56 brazed or otherwise secured to the neck 57 of probe 16. Tube 56 is surrounded by a plastic sleeve 58 having a well 59 at its right hand end providing a sliding snug fit with the shouldered portion of shank 54. An O-ring or other sealing gasket 60 is positioned in the bottom of well 59. In the assembled position of the detachable expansion chamber shown in FIG. 2, which subassembly includes tube 56, probe 16 and plastic sleeve 58 gasket 60 is held snugly captive in well 59 at all times and cannot be accidentally dislodged even should the operator attempt removal of the expansion chamber subassembly while the expansion chamber is pressurized. Moreover, when these parts are assembled, the adjacent ends of the plastic sleeves 52, 58 always lie snugly flush with the adjacent radial faces of the flanged coupling 53.

From the foregoing, it will be recognized that the coolant delivery tube subassembly 40, together with its detachable coupling 42, may be readily and quickly removed at any time after first detaching the two halves of the plastic hand grip housing 12. The operator then applies a tool to kerf 44 and detaches subassembly 40 for servicing or replacement with one having a different size delivery orifice 46. Likewise, it will be recognized that the tissue contact probe or expansion subassembly shown in FIG. 2 and held detachably assembled to barrel 14 by coupling 53,54 may be removed and replaced at any time with another probe subassembly having a differently contoured expansion chamber and heat conducting housing 16.

Figure 4:
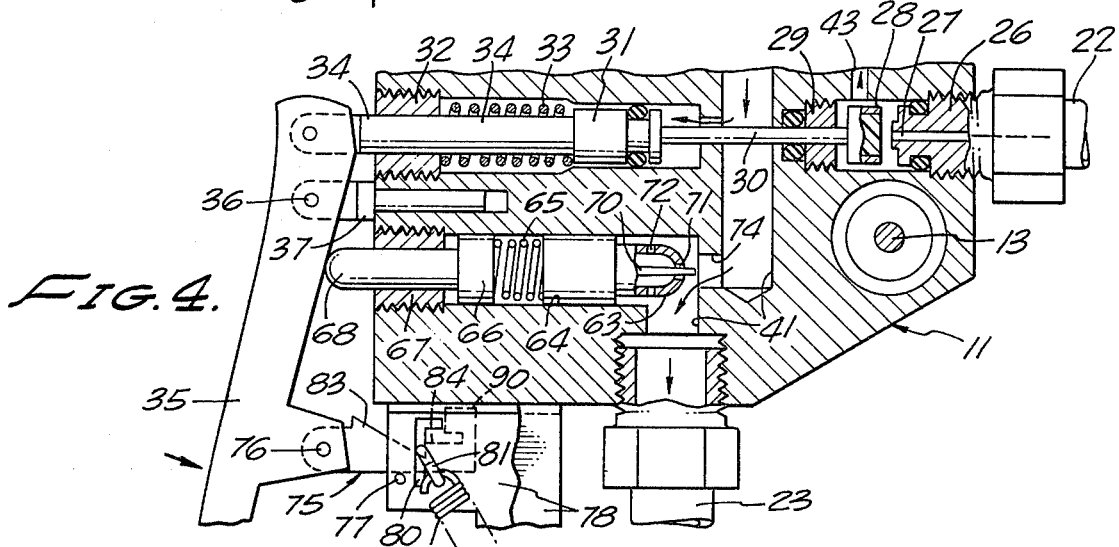
FIG. 4 is a cross-sectional view of a portion of FIG. 3 but showing the operating control locked at the end of the first stage of its movement wherein the device operates in a continuous freezing mode.
Figure 5:
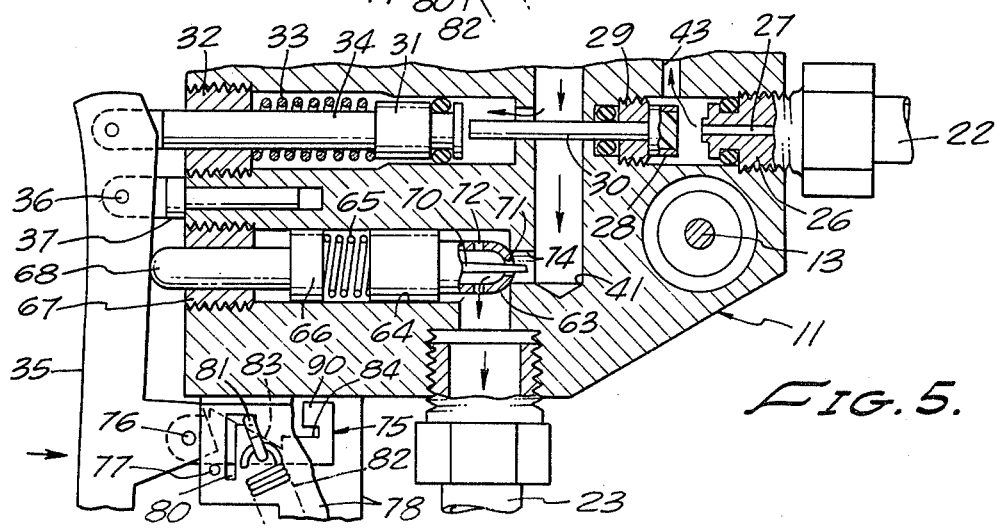
FIG. 5 is a view similar to FIG. 4 but showing the control manually held at the end of its second stage movement to close the exhaust valve and operate the device in the thawing and defrosting modes.

Referring now to FIGS. 3-5 the structural and operating details of the exhaust valve and the operating lever locking means will be described. The normally open exhaust valve comprises a thimble shaped valve 63 slidably mounted in a bore 64 aligned with the port 74 in the exhaust gas passage 41 and discharging into the flexible outlet tube 23. The exhaust valve 63 is constructed to function also as a low pressure regulator. To this end, its outer or left hand end bears against a calibrated spring 65 biasing a plunger 66 slidably supported in a bushing 67. This spring preferably has the same general rate as spring 33 as, for example, 150 lbs. per inch if the fulcrum points for pistons 31 and 66 equidistant from and on the opposite sides of pivot pin 36. The rounded outer end 68 of plunger 66 bears against operating lever 35 closely below its fulcrum 36.

Adjustably supported axially of valve 63 is a fitting 69 (FIG. 3) having a precision tapered restrictor 70 projecting through and preferably well beyond an orifice 71 in the tip end of valve 63. Restrictor 70 provides a low cost mode of manufacturing a calibrated bleed orifice 71 which is the functional equivalent of a 0.006 inch orifice and through which gas in the portion of venting passage 41 upstream from the exhaust valve can escape to the atmosphere during the defrost, warming and thawing modes of operation. It is important that orifice 71 bleed pressurized coolant from the expansion chamber to the atmosphere via the several outlet ports 72 and tube 23 at an appropriate rate to maintain the expansion chamber at a substantial thawing temperature. Thus, orifice 71 should have a flow capacity less than that of the inlet orifice 46 to the expansion chamber as, for example, a flow rate of 0.5 to 2.0 cubic feet per minute when the pressure in the expansion chamber is in the vicinity of 600 psi. Coolant flow through the expansion chamber at this pressure and rate maintains the probe 16 at a substantial supra-freezing temperature effective to thaw frozen tissue quickly and efficiently so long as the exhaust valve 63 is held closed against the outlet end of the exhaust port 74.

It will be noted that the exhaust valve subassembly including valve 63, spring 65 and plunger 66 are floatingly supported in passage 64 of the main body so long as the operating lever 35 is in its normal extended position as shown in FIGS. 1 and 3. Any gas pressure which may develop in the venting passage 41 is effective to force this assembly to its retracted position. In this connection it will be understood that the normal relaxed length of the calibrated spring 65 is that shown in FIGS. 3 and 4.

The mechanism for locking the control lever in its freezing mode position, i.e., at the end of its first stage range movement, comprises a slider member 75 pivoted to lever 35 at 76. The lower edge of slider 75 rides along a support pin 77 mounted crosswise of a pair of brackets 78 brazed at 79 or otherwise secured to the underside of main body 11. The vertical legs of bracket 78 have inverted L-shaped slots 80 loosely supporting the outer ends of a stirrup member 81 best shown in FIG. 6. This stirrup extends transversely of the brackets 78 with its ends projecting through and beyond slots 80 and seating the upper ends of a pair of tension springs 82,82. The stirrup member 81 extends crosswise of the upper edge of member 75 which is provided with a combination locking ramp and detent 83. The stepped lower end of this ramp merges with a horizontal surface 84 on which stirrup 81 rests so long as the operating lever 35 in its extended or non-operating position shown in FIG. 3. As the operating lever 35 is pivoted inwardly about fulcrum 36 stirrup 81 is held stationary in the vertical leg of slots 80. But when trigger 35 reaches the end of its first stage movement, stirrup 81 falls into the notch at the lower end of ramp 83 and locks the operating lever in this position wherein the inlet valve 28 is open. The exhaust valve is moved somewhat closer to the exhaust port 74 but is far short of interfering with the free escape of exhaust gases therepast. Accordingly, the instrument now functions in a continuous freezing mode without need for the operator to apply any pressure on trigger 35.

If the operator next moves the operating lever 35 counterclockwise through its second stage of movement, ramp 83 underrides stirrup 31 and elevates it into the horizontal leg of slots 80 where it is held by springs 82 so long as lever 30 is manually held fully depressed to seat the exhaust valve 63 over outlet passage 74. The very substantial gas pressure then prevailing in the portion of the venting passage 41 upstream from exhaust valve 63 is transmitted to trigger 35 via the pressure regulator spring 65 and the plunger 66 but is countered in major part by the upstream gas pressure acting on piston 31. It wil therefore be appreciated that, by properly proportioning the sizes of the exhaust valve and of piston 31 and the spring rates of spring 33 and 65 together with the proper proportioning of the reaction points of these members on lever 35 relative to its fulcrum 36, the pressure required to be applied to the lower end of lever 35 to retain the instrument in the warming or thawing modes may be reduced to a negligible value readily controlled by one finger of the operator, or even to zero if this should be desired. Preferably, however, a small positive pressure should be required to hold the exhaust valve closed thereby providing a margin of safety by assuring that the main valve 28 will always close unless deliberately held open.

From the foregoing it will be evident the control lever or trigger 35 is readily moved to any position with a minimum of applied pressure. Normally, spring 33 provides a force of 15 lbs which is quite ample to assure closure of inlet valve 28 against a typical maximum tank pressure of 800 psi to 1,000 psi. It follows that this 15 lb. force must be overcome to open valve 28. But owing to the 10 to 12 mechanical advantage provided by trigger 35, the inlet valve is readily opened whereupon a back pressure of approximately 25 psi rapidly develops in chamber 15 and exhaust passage 41. This pressure acts on the floating exhaust subassembly 63, 64, 66 as well as on the servo-piston 31, and is therefore of negligible effect on the trigger because the trigger fulcrum is shown as positioned approximately midway between the piston 31 and exhaust valve 63. Once the trigger is moved to its normal freezing mode position, it can be locked in this position as the notch at the bottom of ramp 83 on slider 75 seats stirrup 81 thereby locking the trigger in the freezing mode position.

If trigger 35 is fully depressed to the defrost or thawing mode position, exhaust valve 63 is closed and the back pressure in passage 41 rapidly increases to approximately 625 psi, or other pressure permitted by the pressure regulator forming a part of the exhaust valve subassembly. This pressure acts on and tends to open the exhaust valve and upon the somewhat larger inner end of the servo-piston 31. Since these two forces oppose one another on the opposite sides of the trigger fulcrum 36, it is apparent that the operator need apply a very small and almost negligible force on the trigger to maintain the defrost or thawing modes. It is therefore a simple matter to design the instrument to operate with either a very small or a somewhat larger applied force merely by selecting the proper relative sizes of exhaust port 74 and servo-piston 31.

Two modified version of the exhaust valve are shown in FIGS. 7 and 8 respectively, the same or similar parts in FIG. 7 being designated by the same characters as in FIGS. 1–6 but distinguished by the addition of a prime and the characters in FIG. 8 likewise being the same as those employed in FIGS. 1–6 but distinguished therefrom by the addition of a double prime.

In FIG. 7, the spring 65 has been omitted together with its function with the result that the floating exhaust valve 63' bears directly against the inner end of plunger 66'. Accordingly, the FIG. 7 embodiment lacks means for automatically regulating the pressure in the exhaust passage 41' during defrost and thawing modes of operation. Except for the pressure regulating capability, this embodiment has all of the other features of the first embodiment.

In the FIG. 8 embodiment the flow restrictor passage 71" is in parallel with the exhaust valve port 74". Additionally, this modified restrictor passage lacks the tapered spindle 70 for adjusting the size of passage 71" serving to bypass warm gas around exhaust valve 63" when the latter is closed during the defrost and thawing modes. It will also be noted that the low pressure regulator spring 65" is interposed between the adjacent ends of exhaust valve 63" and piston 66". Accordingly, this embodiment functions to regulate and limit the maximum pressure in exhaust passage 41" during the thawing mode. Also it will be understood that restrictor passage 71" functions in the same manner as the corresponding passage 71' in FIGS. 1–6 to the limit the escape of gas past the closed exhaust valve to an amount providing effective and continuous thawing at the expansion chamber 15,16 so long as the exhaust valve is held closed.

OPERATION

The instrument is placed in operation by opening the main supply valve 19 at the top of supply tank 18 allowing pressurized gas, such as nitrous oxide or carbon dioxide typically stored at 800–1000 psi, to flow to the instrument through supply tube 22. Initially, entrance of this high pressure gas into the instrument is blocked by the normally closed inlet valve 28 which is normally held closed by the heavy duty calibrated spring 33. Accordingly, and so long as valve 28 remains closed, the entire instrument is free of high pressure gas unless and until the operating lever or trigger 35 is depressed by the operator, an operation normally conducted only while the instrument is gripped by a handgrip 12 with one finger encircling trigger 35. As this trigger is depressed toward handgrip 12, thereby compressing spring 33 and allowing the high pressure gas to open inlet valve 28 and flow to the expansion chamber via the delivery tube 40 and the inlet orifice 46.

Initial operation of the instrument is normally in the freezing mode initiated as the operator depresses the trigger 35 until stirrup 81 rides off the horizontal step 84 of slider 75 and falls into the bottom of ramp 83. Springs 82 and stirrup 81 then cooperate, as shown in FIG. 4, in locking the trigger in the freezing mode. Accordingly, no effort is required on the part of the operator to maintain the instrument in the freezing mode and the high pressure gas continues to expand into the expansion chamber 15 to produce low level freezing. Expanded gas escapes to the atmosphere through the escape passage 41, exhaust gas port 74, past the normally open exhaust valve 63, and along gas outlet tube 23 and exits to the atmosphere via muffler 20. The back pressure of the escaping gas, typically 25 psi, holds the gas valve 63 firmly open for self-apparent reasons.

After a freezing period of a desired duration, the operator has a choice of (1) discontinuing the operation of the device completely, (2) going into a brief defrost mode, or (3) going immediately to a continuous thawing mode. If he wishes to discontinue the operation completely, he simply pulls the trigger toward handgrip 12 to its fully retracted position and then releases it. As the trigger approaches this fully retracted position, ramp 83 underrides stirrup 81 thereby elevating it through the vertical leg of slots 80 onto and into the horizontal leg where it is temporarily held by spring 82 in the manner clearly shown in FIG. 5. Exhaust valve 63 is now closed against the exhaust port 74 with the result that the pressure in the gas escape passage 41 upstream from the exhaust valve quickly increases toward the supply pressure of 800 psi. Accordingly, if the operator now relaxes his grip on trigger 35 the high pressure gas in passage 41 tends to unseat exhaust valve 63 and to urge the trigger back to its extended position along with slider 75. As slider 75 moves to the left, its upturned end 90 engages stirrup 81 and shifts it out of the horizontal leg of slots 80 and allows the stirrup to fall onto the underlying step 84 of the slider. Accordingly, trigger 35 is now free to return to its original extended position shown in FIG. 3 as the exhaust valve 63 returns to its fully opened position and spring 33 reseats inlet valve 28 in closed position.

Now let it be assumed the operator wishes to operate the instrument through a short defrosting cycle at the end of the freezing mode. In this event, he merely depresses trigger 35 to the position shown in FIG. 5 to hold the exhaust valve closed for a desired short defrost period. Again, the expanded gas cannot escape through the closed port 74 and the gas pressure in passage 41 quickly stabilizes at about 600 psi. This pressure exists in the chamber containing piston 31 and counteracts a major portion of the pressure exerted by spring 33. The trapped pressurized gas also acts on the exhaust 63 and if the pressure increases beyond the calibrated strength of the regulator spring 65, the exhaust valve opens momentarily to relieve the excess pressure. At all times, however, a portion of the trapped gas in passage 41 continues to escape to the atmosphere via the bleeder orifice 71, ports 72 and exhaust hose 23. This gas flow serves to maintain a steady flow of warm gas into and through the expansion chambers. Owing to this steady flow of warm high-density gas and the very low level expansion permitted in the expansion chamber, the temperature of this chamber quickly rises with the result that probe 16 quickly defrosts and transmits substantial quantities of heat into tissue in contact therewith. Defrosting continues only so long as the trigger is held depressed to the position shown in FIG. 5 and is discontinued simply by releasing the low pressure required to maintain the trigger in the defrosting mode.

Assuming now that the operator wishes to operate the instrument in a continuous thawing mode at the end of a freezing mode, he simply depresses the trigger for the duration of the desired continuous thawing cycle. As mentioned above, very light pressure suffices to hold trigger 35 fully depressed. Experience has shown that a flow of ½ to 2 cubic feet of gas per minute through the expansion chamber and past the restrictor orifice 71 is effective to maintain the expansion chamber at a temperature of about 45° F. indefinitely and so long as the supply source 18 contains pressurized gas at a suitable operating pressure such as 650 psi or above.

It will be readily recognized from the foregoing that the invention instrument is admirably suited for conducting a series of freeze, thaw cycles in rapid sequence thereby producing rapid and highly effective destruction of live tissues to depths not previously feasible. The efficacy of the operation is promoted by scraping away destroyed tissue at the end of a thawing cycle thereby enabling the probe 16 to be placed in direct contact with the next lower layer of live tissue to be necrotized.

While the particular cryogenic device selectively operable in a continuous freezing mode, a continuous thawing mode or a combination thereof herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

I claim:

1. A cryogenic device selectively operable in a continuous freezing mode and in a continuous warming mode at the user's option comprising in combination:
   means connecting a source of high pressure gas for flow solely in series first through an expansion orifice into an expansion chamber, then through a pre-set calibrated second orifice smaller than said first orifice, and then to the atmosphere,
   exhaust gas valve means movable between open and closed positions operatively associated with said pre-set second orifice to control the flow of gas emanating solely from said expansion chamber to provide a freezing mode when said exhaust valve means is open and to provide a continuous suprafreezing warming mode when said exhaust valve means is in closed position, a manually operable cutoff valve located between said source and said expansion orifice controlling the flow of pressurized gas from said source to said expansion orifice, a spring cooperating with said cutoff valve operable to close said cutoff valve in opposition to the pressure of said gas source, and means in communication with pressurized gas between said expansion orifice and said exhaust valve means responsive to the pressure thereof when said device is operating in said warming mode and effective to counteract a substantial portion of the strength of the spring of said cutoff valve so long as said device is operating in said warming mode.

2. A cryogenic device as defined in claim 1 characterized in that said manually operable cutoff valve includes means permitting said manual means to move in one direction independently of said cutoff valve means.

3. A cryogenic device as defined in claim 1 characterized in that said exhaust valve means is operable to provide successive continuous freezing and warming modes each of a selected duration.

4. A cryogenic device as defined in claim 1 characterized in that said exhaust valve means is operable to cycle said freezing and warming modes to flow one another without delay and in time delayed sequence at the user's option.

5. A cryogenic device as defined in claim 1 characterized in that said second orifice has a flow capacity of the order of 0.5 to 2.0 cfm when the gas pressure in said expansion chamber is in the vicinity of 600 psi.

6. A cryogenic device selectively operable in a continuous freezing mode and in a continuous warming mode at the user's option, comprising:
   means providing a pressurized gas expansion chamber having a first gas expansion orifice opening thereinto from a high pressure source of gas, said expansion chamber being supplied with high pressure gas solely via said first orifice during both the freezing and the warming operating modes of said device;
   exhaust passage means leading from said expansion chamber to the atmosphere and including (a) exhaust valve means movable between open and closed positions and (b) second gas expansion orifice means of substantially smaller predetermined flow capacity than said first expansion orifice and at a rate effective to bleed pressurized gas to the atmosphere from said expansion chamber when said exhaust valve means is in the closed position thereof at a rate such that the flow of said pressurized gas through said expansion chamber is effective to maintain said expansion chamber is a warming mode so long as said exhaust valve means is in said closed position; and
   the expansion of said pressurized gas into said expansion chamber through said first orifice means being effective to maintain said chamber in a freezing mode so long as said exhaust valve means remains open.

7. A cryogenic device as defined in claim 6 characterized in the provision of a spring-biased gas inlet valve controlling the flow of pressurized gas to said first orifice, manually operable means for said inlet valve having spring means sufficiently strong to close said inlet valve and including means responsive to pressurized gas in said expansion chamber when operating in said warming mode to counteract a major portion of the strength of said spring means thereby to minimize the force required to manipulate said manually operable means.

8. A cryogenic device as defined in claim 7 characterized in that said manually operable inlet valve means controlling the flow of gas to said expansion chamber via said first orifice is movable in the same direction through first and second stages, said manually operable inlet valve means being operable in said first stage to open said inlet valve means and operable in said second stage to operate said exhaust valve means toward the closed position thereof independently of said inlet valve means.

9. A cryogenic device as defined in claim 8 characterized in the provision of detent means operable to secure said inlet valve means in open position at the end portion of said first stage movement and operable to release said inlet valve means as said manually operable means is released after being operated through said second stage to move said exhaust valve means toward the closed position thereof.

10. A cryogenic device as defined in claim 7 characterized in the said manually operable inlet valve means is operable to shift said exhaust valve means to a position effective to throttle said escape of gas therepast to a rate effective to maintain said expansion chamber in a warming mode and filled with warm pressurized coolant at a temperature substantially above freezing.

11. A cryogenic device as defined in claim 7 characterized in the provision of means for positively holding said inlet valve in a cooling mode position wherein said inlet valve and said exhaust valve means are both open.

12. A cryogenic device as defined in claim 7 characterized in that said manually operable valve means includes push-push means operable upon being moved a first predetermined distance to move said inlet valve to the open position thereof and including means to lock said inlet valve open, and said push-push means including means responsive to movement of said manually operable means through a second predetermined distance to operate said exhaust valve to a position placing said expansion chamber means in a continuous warming mode filled with pressurized coolant gas at a thawing temperature.

13. A cryogenic device as defined in claim 7 characterized in the provision of means responsive to pressurized coolant on the outlet side of said inlet valve, when open, to oppose a major portion of the strength of said spring-biased inlet valve whereby a relatively small force applied to said manually operable means suffices to hold said inlet valve open.

14. A cryogenic device as defined in claim 13 characterized in that said spring-biased inlet valve is effective to close said inlet valve in opposition to the pressurized coolant immediately upon the release of said manually operable means.

15. A cryogenic device as defined in claim 6 characterized in the provision of a poppet valve controlling the flow of pressurized gas to said first orifice, springbiased manually operable means having a lost motion connection with said poppet valve and the spring of which is strong enough to close said poppet valve against the pressure of said high pressure source, and said manually operable means including means in communication with said pressurized gas and effective when said device is operating in said warming mode to substantially counteract said spring and reduce the requisite operating force applied to said manually operable means to maintain said device in said warming mode.

16. A cryogenic device as defined in claim 15 characterized in that said manually operable means includes means for opening said poppet valve without closing said exhaust valve means.

17. A cryogenic device as defined in claim 6 characterized in the provision of manually operable inlet valve means for controlling the flow of said gas to said first orifice and provided with spring means normally holding the same closed, and means for locking said inlet valve in open position.

18. A cryogenic device as defined in claim 17 characterized in that said manually operable inlet valve means includes means operable through an initial stage to open said inlet valve means and operable through a further stage to operate said exhaust means to restrict the escape of gas to the atmosphere.

19. A cryogenic device as defined in claim 18 wherein said exhaust valve means is operable when closed to restrict the escape of gas to the atmosphere to that gas flowing to the atmosphere through said relatively small second orifice, and said manually operable means being selectively operable in a freezing and in a suprafreezing mode and sequentially in first one mode and then in the other mode depending upon the manipulation of said manually operable means.

20. A cryogenic device as defined in claim 18 characterized in the provision of means exposed to pressurized gas flowing from said relatively large first orifice toward said relatively small second orifice and responsive to said pressurized gas to oppose said spring urging said inlet valve means closed so long as said cryogenic device is operating in said warming mode.

21. A cryogenic device as defined in claim 6 characterized in the provision of means for adjusting the size of said second orifice to vary the warming mode temperature of said device.

22. A cryogenic device as defined in claim 6 characterized in that said second orifice includes a flow passage having a tapering plug extending axially thereof and cooperating therewith to form a minute annular flow passage for gas escaping to the atmosphere.

23. A cryogenic device as defined in claim 22 characterized in that said tapering plug extends substantially beyond the entrance end of said second orifice and into the pressurized gas flowing toward said second orifice.

24. A cryogenic device as defined in claim 22 characterized in the provision of means for adjusting said tapering plug axially of said small orifice to vary the gas flow therethrough when said exhaust valve means is closed.

25. A cryogenic device as defined in claim 6 characterized in that said exhaust valve means includes means for limiting the maximum gas pressure in said expansion chamber to a predetermined maximum pressure so long as said device is operating in said continuous warming mode regardless of the pressure of said source of high pressure gas.

26. A cryogenic device as defined in claim 6 characterized in that said second orifice has a flow capacity of the order of 0.5 to 2.0 cfm.

27. A cryogenic device comprising in combination:
a generally L-shaped main body one leg of which is provided at the free end thereof with a gas expansion chamber of heat conductive material and the other leg of which includes a handgrip;
tubular means extending into the outer end of said handgrip for conveying pressurized gas in series from a source of pressurized gas to and through said main body, said expansion chamber and for thereafter venting the same to the atmosphere and including a cutoff valve controlling the flow of pressurized gas into said tubular means, first orifice means in said tubular means opening into said expansion chamber, a normally open exhaust valve for venting gas to the atmosphere from said expansion chamber, and second orifice means smaller than said first orifice means continually open to the atmosphere, and gas flow control means including manually operable trigger means selectively manipulatable by the operator while grasping said handgrip (1) for opening said cutoff valve without closing said exhaust valve thereby to operate said expansion chamber in a cooling mode as long as said exhaust valve remains open and (2) for closing said exhaust valve without closing said cutoff valve to operate said expansion chamber in a warming mode so long as said exhaust valve remains closed and said cutoff valve remains open, said cutoff valve including spring means effective when not manually restrained to reclose the same against the gas supply pressure, and means responsive to the gas pressure between said first and second orifices for partially countering the effectiveness of said spring means to close said cutoff valve so long as said exhaust valve is closed.

28. A cryogenic device as defined in claim 27 characterized in that said trigger means includes means for locking said cutoff valve open, and means for deactivating said locking means for said cutoff valve as an incident to the closing and reopening of said exhaust valve.

29. A cryogenic device as defined in claim 27 characterized in that said trigger means is pivotally supported on said main body near one end thereof and operable through a first range effective to open said cutoff valve and then in the same direction through a second range effective to close said exhaust valve.

30. A cryogenic device as defined in claim 27 characterized in that said trigger means includes locking means for locking said cutoff valve means open when moved through a first range and additional means operable when said trigger means is moved through a second range to deactivate said locking means and permit reclosing of said cutoff valve and the return of said trigger means to the initial position thereof.

31. A cryogenic device as defined in claim 27 characterized in that said tubular means with said first orifice is removable as a unit from said main body, and fastener means for holding said tubular means detachably assembled to said main body independently of said means for conveying pressurized gas thereto.

32. A cryogenic device as defined in claim 27 characterized in that said expansion chamber includes separable coupling means holding the same coupled to the outer end of said one leg in a fluid tight manner, said coupling including a sealing gasket surrounding and held captive between a threaded shank and a threaded tubular member embracing said threaded shank and each forming cooperating parts of said coupling.

33. A cryogenic device as defined in claim 27 characterized in that said tubular means comprises a tubular subassembly extending axially along the interior of said one leg of said L-shaped main body, said tubular subassembly having fluid tight coupling means holding the same detechably coupled to said one leg adjacent the junction thereof with said handgrip leg and including means for supplying pressurized gas thereinto laterally of and via said fluid tight coupling.

34. A cryogenic device having a coolant expansion chamber provided with a gas venting passage for discharging gas to the atmosphere via an exhaust valve, means including an expansion orifice for supplying pressurized coolant to said expansion chamber under the control of an inlet valve normally held closed by a spring, means responsive to gas pressure in said venting passage when said exhaust valve is closed to materially counteract the action of said spring so long as said exhaust valve is closed, and manually operable means operatively connected to said inlet valve and to said exhaust valve selectively manipulatable to open said inlet valve without closing said exhaust valve and to close said exhaust valve without closing said inlet valve.

35. A cryogenic device as defined in claim 34 characterized in that said manually operable means includes lever means having a fulcrum located between a separate load bearing cooperating point for said inlet valve and for said exhaust valve and effective upon movement through a first range of said lever means in one direction to open said inlet valve without materially varying the escape of coolant past said open exhaust valve.

36. A cryogenic device as defined in claim 35 characterized in that said device includes means in communication with said venting passage having a substantially smaller flow capacity than said inlet orifice and effective to maintain said expansion chamber temperature in a warming mode so long as said exhaust valve is closed, and said lever means being effective to close said exhaust valve when pivoted in the same direction through a second range.

37. A cryogenic device as defined in claim 35 characterized in the provision of means automatically operable to lock said lever means against retrograde movement at the end of said first range.

38. A cryogenic device as defined in claim 37 characterized in the provision of means for deactivating said locking means as said lever means is moved along said second range.

39. A cryogenic device as defined in claim 37 characterized in the provision of means for deactivating said locking means for said lever means in response to movement of said lever means a predetermined distance into said second range and prior to the closing of said exhaust valve whereby said cryogenic device is selectively operable in a freezing mode and in a warming mode both sequentially and solely in either a freezing or a warming mode depending on manual manipulation of said lever means.

40. A cryogenic device as defined in claim 34 characterized in that said exhaust valve includes spring means operable to permit said exhaust valve to vent coolant gas therepast to the atmosphere when the pressure in said gas venting passage exceeds a predetermined value even though the person operating said cryogenic device endeavors to maintain said exhaust valve closed.

41. A cryogenic device as defined in claim 34 characterized in that said device includes means to limit the maximum gas pressure in said expansion chamber to a predetermined value when said exhaust valve is closed.

42. A cryogenic device comprising:
a main body having a heat insulated tube extending therefrom which tube has a distal end and a proximal end;
a cryogen expansion chamber embracing and in communication with the distal end of said tube;
a cryogen delivery unit mounted lengthwise of the interior of said tube having a cryogen discharge orifice at the distal end thereof for discharging pressurized cryogen gas into said expansion chamber;
a passage for venting cryogen to the atmosphere from said expansion chamber;
inlet valve means for said cryogen delivery unit spring-biased to the closed position thereof against the prevailing pressure of a supply source of pressurized cryogen and which valve means opens is response to an abnormal increase in the cryogen supply pressure thereby releasing cryogen into said expansion chamber and thence to the atmosphere via said cryogen venting passage.

exhaust valve means in said venting passage means including a valve seat and movably supported valve means on the discharge side of said valve seat;

movably supported manual control means common to said inlet valve means and said exhaust valve means selectively operable to open said inlet valve means without closing said exhaust valve means and to close said exhaust valve means without closing said inlet valve means; and said inlet valve means including means actuable by pressurized coolant in said venting passage to oppose the closing of said spring-biased inlet valve means so long as said inlet valve means is open.

43. A cryogenic device as defined in claim 42 characterized in that said inlet valve means includes means actuable by pressurized coolant in said venting passage between said expansion chamber and said exhaust valve means to neutralize a major portion of the effectiveness of the spring biasing said inlet valve toward closed position when said exhaust valve means is closed.

44. A cryogenic device as defined in claim 42 characterized in the provision of calibrated spring means between said control means and said exhaust valve means operable to permit said exhaust valve means to open automatically and limit the maximum pressure in said expansion chamber to a predetermined value regardless of the pressure of the gas source so long as the operator endeavors to hold said exhaust valve means closed.

* * * * *